(12) United States Patent
Yang et al.

(10) Patent No.: US 9,462,978 B2
(45) Date of Patent: *Oct. 11, 2016

(54) SENSING DEVICE

(75) Inventors: Chang-Ming Yang, Miaoli (TW); Tzulin Yang, Taipei (TW); Hao Yang, Taipei (TW)

(73) Assignee: Ming Young Biomedical Corp., Miaoli (TW)

( * ) Notice: Subject to any disclaimer, the term of this patent is extended or adjusted under 35 U.S.C. 154(b) by 205 days.

This patent is subject to a terminal disclaimer.

(21) Appl. No.: 13/146,147

(22) PCT Filed: Jan. 24, 2009

(86) PCT No.: PCT/CN2009/000118
§ 371 (c)(1),
(2), (4) Date: Jul. 25, 2011

(87) PCT Pub. No.: WO2010/083630
PCT Pub. Date: Jul. 29, 2010

(65) Prior Publication Data
US 2011/0282164 A1 Nov. 17, 2011

(51) Int. Cl.
*A61B 5/00* (2006.01)
*A61B 5/01* (2006.01)
(Continued)

(52) U.S. Cl.
CPC ............... *A61B 5/6892* (2013.01); *A61B 5/01* (2013.01); *A61B 5/1038* (2013.01); *A61B 5/11* (2013.01); *A61B 5/6804* (2013.01); *A61B 5/6807* (2013.01); *B60N 2/002* (2013.01); *B60N 2/58* (2013.01); *B60N 2/60* (2013.01); *G06F 3/011* (2013.01); *G06F 3/014* (2013.01);
(Continued)

(58) Field of Classification Search
CPC ......... G06F 3/014; G06F 3/011; B60N 2/60; A61B 5/01; A61B 5/6804–5/6807; A61B 5/1117; A61B 5/1038; A61B 2562/0247; A61B 2562/026
See application file for complete search history.

(56) References Cited

U.S. PATENT DOCUMENTS 4,415,781 A 11/1983 Frame et al.
4,494,553 A * 1/1985 Sciarra et al. ................ 600/534
(Continued)

FOREIGN PATENT DOCUMENTS

CN 1666308 A 9/2005
JP S62272415 A 11/1987
(Continued)

OTHER PUBLICATIONS

International Search Report w/translation from PCT/CN2009/000118 dated Oct. 29, 2009 (6 pages).
(Continued)

*Primary Examiner* — William Thomson
*Assistant Examiner* — Shirley Jian
(74) *Attorney, Agent, or Firm* — Osha Liang LLP

(57) ABSTRACT

A sensing device comprises a substrate material layer and a plurality of sensors provided on the substrate material layer. The plurality of sensors is electrically connected to form a loop. The loop has two output ends. There is a loop output value between the two output ends. The loop output value varies when the sensors are subjected to an external force. Each sensor has one induction value. The induction value of each sensor is different from each other. A total induction value of any one or more sensors is different from a total induction value of the other one or more sensors.

19 Claims, 8 Drawing Sheets

(51) Int. Cl.

| | | |
|---|---|---|
| *A61B 5/103* | (2006.01) | |
| *A61B 5/11* | (2006.01) | |
| *B60N 2/00* | (2006.01) | |
| *B60N 2/58* | (2006.01) | |
| *B60N 2/60* | (2006.01) | |
| *G06F 3/01* | (2006.01) | |

(52) U.S. Cl.
CPC ..... *A61B 5/1117* (2013.01); *A61B 2562/0247* (2013.01); *A61B 2562/0261* (2013.01)

(56) References Cited

U.S. PATENT DOCUMENTS

| | | | | |
|---|---|---|---|---|
| 5,235,967 | A * | 8/1993 | Arbisi et al. | 601/101 |
| 6,155,120 | A | 12/2000 | Taylor | |
| 6,210,771 | B1 | 4/2001 | Post et al. | |
| 6,381,482 | B1 * | 4/2002 | Jayaraman et al. | 600/388 |
| 6,493,933 | B1 | 12/2002 | Post et al. | |
| 6,504,531 | B1 * | 1/2003 | Sandbach | 345/173 |
| 6,505,522 | B1 * | 1/2003 | Wilssens | G01L 1/205 |
| | | | | 73/862.51 |
| 6,551,252 | B2 * | 4/2003 | Sackner et al. | 600/536 |
| 6,600,120 | B1 | 7/2003 | Marmaropoulos et al. | |
| 6,642,467 | B2 * | 11/2003 | Farringdon | 200/511 |
| 6,687,523 | B1 * | 2/2004 | Jayaramen et al. | 600/388 |
| 6,714,117 | B2 * | 3/2004 | Sandbach | 338/101 |
| 6,729,025 | B2 * | 5/2004 | Farrell et al. | 29/854 |
| 6,809,662 | B2 | 10/2004 | Wong-Lam et al. | |
| 6,826,968 | B2 | 12/2004 | Manaresi et al. | |
| 6,944,920 | B2 * | 9/2005 | Browne et al. | 24/442 |
| 7,070,571 | B2 * | 7/2006 | Kramer et al. | 600/595 |
| 7,102,614 | B2 * | 9/2006 | Sandbach et al. | 345/156 |
| 7,145,432 | B2 | 12/2006 | Lussey et al. | |
| 7,301,351 | B2 * | 11/2007 | Deangelis et al. | 324/687 |
| 7,602,301 | B1 * | 10/2009 | Stirling et al. | 340/573.1 |
| 7,762,953 | B2 * | 7/2010 | Derchak et al. | 600/300 |
| 7,825,814 | B2 * | 11/2010 | Lokhorst | A61B 5/11 |
| | | | | 340/573.1 |
| 7,861,605 | B2 * | 1/2011 | Ogawa | 73/862.69 |
| 8,331,097 | B2 * | 12/2012 | Yang et al. | 361/749 |
| 8,945,328 | B2 * | 2/2015 | Longinotti-Buitoni et al. | 156/234 |
| 8,948,839 | B1 * | 2/2015 | Longinotti-Buitoni et al. | 600/382 |
| 2002/0005342 | A1 | 1/2002 | Farringdon | |
| 2002/0076948 | A1 | 6/2002 | Farrell et al. | |
| 2002/0180578 | A1 | 12/2002 | Sandbach | |
| 2002/0193707 | A1 | 12/2002 | Atlas et al. | |
| 2003/0107504 | A1 | 6/2003 | Wong-Lam et al. | |
| 2005/0065552 | A1 * | 3/2005 | Yu | 607/2 |
| 2006/0254811 | A1 * | 11/2006 | Kirstein et al. | 174/256 |
| 2007/0171024 | A1 * | 7/2007 | Yang et al. | 338/2 |
| 2008/0230363 | A1 | 9/2008 | Yang et al. | |
| 2008/0287770 | A1 * | 11/2008 | Kurzweil et al. | 600/388 |
| 2009/0227857 | A1 * | 9/2009 | Rowe et al. | 600/392 |
| 2009/0312826 | A1 * | 12/2009 | Penny et al. | 607/149 |
| 2010/0005908 | A1 * | 1/2010 | Ogawa | 73/862.69 |
| 2010/0033362 | A1 | 2/2010 | Kitami | |
| 2010/0296257 | A1 | 11/2010 | Yang et al. | |
| 2011/0105861 | A1 * | 5/2011 | Derchak et al. | 600/301 |
| 2013/0041272 | A1 * | 2/2013 | Guillen Arredondo et al. | 600/509 |
| 2013/0085420 | A1 * | 4/2013 | Feinstein | 601/5 |
| 2013/0338472 | A1 * | 12/2013 | Maci Barber et al. | 600/388 |

FOREIGN PATENT DOCUMENTS

| | | | | |
|---|---|---|---|---|
| JP | 04-047617 | A | 2/1992 | |
| JP | 3024717 | U | 5/1996 | |
| JP | H10144168 | A | 5/1998 | |
| JP | 3079412 | U | 8/2001 | |
| JP | 2002-029381 | A | 1/2002 | |
| JP | 2007035586 | A | 2/2007 | |
| JP | 2008123918 | A | 5/2008 | |
| JP | 2008181806 | A | 8/2008 | |
| WO | 2007/033520 | A1 | 3/2007 | |
| WO | WO 2008039082 | A2 * | 4/2008 | A61B 5/0205 |
| WO | 2009/033361 | A1 | 3/2009 | |
| WO | 2009/033362 | A1 | 3/2009 | |

OTHER PUBLICATIONS

Notice of Reasons for Rejection (Official Action) issued on Jun. 11, 2013, by the Japan Patent Office in related Japanese Patent Application No. JP2011-546564, with Google English machine translation (11 pages).

Patent Abstracts of Japan English Abstract for Japanese Publication No. 04-047617, published Feb. 17, 1992 (1 page).

Patent Abstracts of Japan English Abstract for Japanese Publication No. 2002-029381, published Jan. 29, 2002 (1 page).

EPO Communication dated Feb. 18, 2014, with Extended European Search Report, issued by the European Patent Office in corresponding European Patent Application No. EP-09838597.4 (9 pages).

Office Action in corresponding Japanese Patent Application No. 2015-186253, dated Jul. 7, 2016 (13 pages).

\* cited by examiner

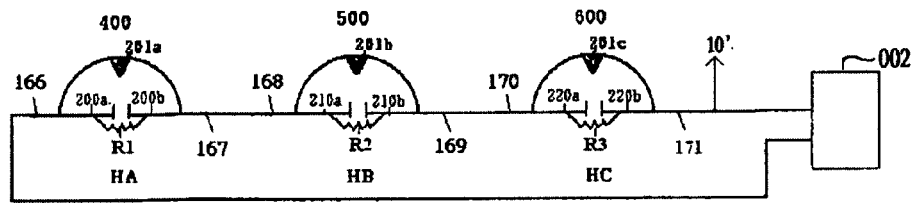
FIG. 12
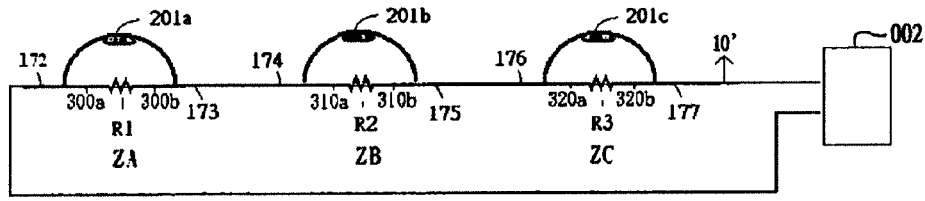
FIG. 13
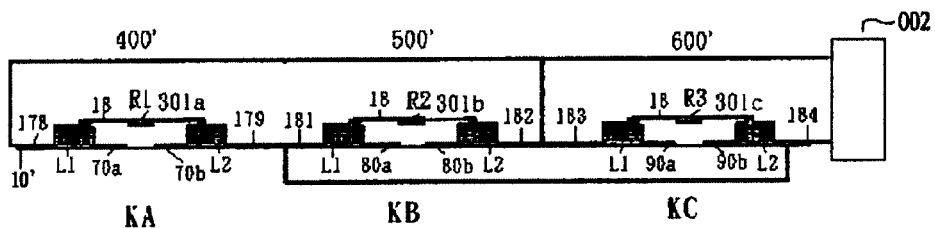
FIG. 14
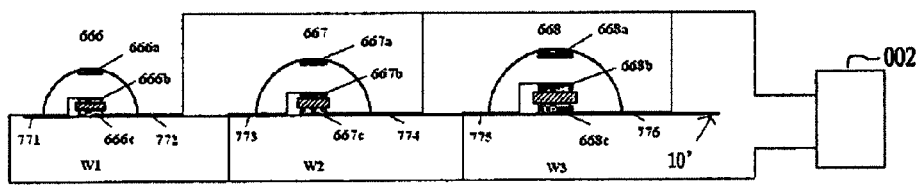
FIG. 15
FIG. 16
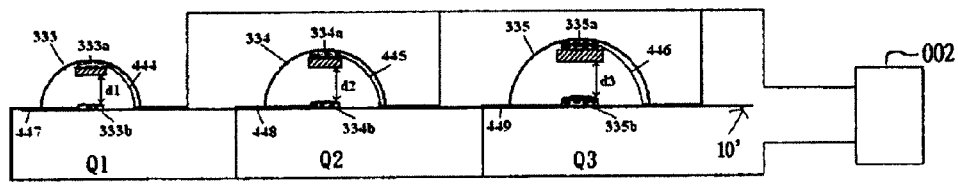

SENSING DEVICE

TECHNOLOGICAL FIELD

This invention relates to sensing apparatus, especially apparatus with few output terminals and easy to operate.

TECHNOLOGICAL BACKGROUND

There are many sensors made on textile to detect signals from human or animals. These sensors need to be connected to transmission wires and signal processors for further analysis, especially pressure sensors and strain gauges. There are many types of pressure sensors and strain gauges. For example, PCT/CN2005/001520 discloses an electronic device having a sensor array for detecting pressure points. However, each sensor in the array is identical. Therefore, each sensor has to be connected to the signal processor via its own transmission wires in order for the signal processor to distinguish individual pressure points. It is the same situation in PCT/CN2008/001570, which discloses clothing materials having separate inductive areas, and PCT/CN2008/001571, which discloses clothing materials for forming electronic components.

FIG. 1 shows a side view schematic diagram of a prior art sensing apparatus. The sensing apparatus has three pressure sensors A, B, and C on textile (clothing material) connected to processor 002 in parallel. Sensor A has two output terminals 1 and 2. Terminal 2 is connected to sensing area "111a", and terminal 1 is connected to sensing area "122a". Sensor B has output terminals 3 and 4. Terminal 4 is connected to "111b" and terminal 3 is connected to "122b". Sensor C has output terminals 5 and 6. Terminal 6 is connected to "111c" and terminal 5 is connected to "122c". The sensors A, B, and C connect with the signal processor 002 via four connection points. One of the connection points is common to output terminals 1, 3, and 5. The other three connection points are separately connected to output terminals 2, 4, and 6. While not pressed, the sensors A, B, and C are in open-circuit state such that the impedance between the terminals is very high. When appropriate force is applied, these sensors are in close-circuit state and the impedance is approximately zero. With such prior art sensing apparatus, when user presses any sensor, the processor 002 would sense the signal. However, in such a sensing apparatus, the signal processor has four connecting points connecting with four terminals from three sensors. That is, there are four independent signal transmission wires disposed on clothing materials, increasing the costs of such materials. It is complicated to arrange output wires on a cloth material, because unlike a circuit board, one cannot implement multi-layer circuits on a cloth or a leather material. In addition, more wires on a cloth material increase the chance of malfunction. After washing, if one of the wires breaks, the sensing apparatus would not work. Furthermore, it is not easy to maintain isolation between the wires. Such materials are not environmental friendly and are prone to short circuits and broken circuits.

The values sensed by pressure sensor A can be adjusted by changing the structure, thickness, or materials in the upper sensing area 111 to produce different pressure responses. For example, the materials can be cotton, nylon, latex rubber, silicone rubber, synthesized sponge, etc. The materials of the sensing area 111a or 122b can be conductive materials such as steel fiber, steel wire, silver fiber, silver wire, conductive rubber, copper fiber, nickel fiber, gold wire, graphite fiber, or conductive plastics.

Referring to FIG. 2, which shows a schematic diagram of a prior art sensing apparatus applied on bed sheet or cushion. Fifteen pressure sensors are fixed on bed sheet to measure posture changes during sleep, e.g., supine, lateral, prone, spasm or no movements. The sensing apparatus can also detect breathing and the time the sleeper lies on bed and gets up. This apparatus has sixteen transmission wires to connect to the input terminals of the signal processor 002. This is tedious to manufacture.

Referring to FIG. 3, which shows another schematic diagram of a prior art sensing apparatus. The bed sheet has three independent signal transmission wires arranged in the X axis and five independent signal transmission wires arranged in the Y axis. The processor 002 connects with eight signal transmission wires. The circuit is complicated and the signal processor 002 cannot get all 15 point signals simultaneously.

Referring to FIG. 4, which shows a schematic diagram of a prior art sensing apparatus. The garment has eight joints (moving locations) on both elbows, shoulders, knees, and hips. There are nine signal transmission wires to connect with the input terminals of the signal processor 002. The lay out design of the wires on the garment is complicated. Its cost is high. With more wires on a garment, there are more chance for wire breakage and it is more difficult to isolate these wires. The materials are not environmental friendly, and they are prone to short circuits or broken circuits.

Referring to FIG. 19, which shows a schematic diagram of a prior art sensing apparatus applied on belt. This belt can detect breathing. Five strain gauges with different tension thresholds (100g, 150g, 200g, 250g, and 300g force thresholds) need six output terminals to connect to the input terminals on the signal processor 002.

In addition, related prior art includes the following:

1. U.S. Pat. No. 6,826,968 discloses cloth materials having sensing devices that use variations of capacitances to detect pressure. As discussed above, assuming N wires in the X axis and M wires in the Y axis, it would need N plus M terminals to connect to the input terminals of a signal processor, which is inconvenient.

2. U.S. Pat. No. 6,210,771 discloses cloth materials having circuit wires running in two orthogonal directions. The circuit wires crisscross; it is difficult to implement. If there is any problem, it would be difficult to determine which element is at fault. More conductive wires on a cloth would make it heavier, and would also make it more likely to fail based on statistics.

3. U.S. Pat. No. 6,729,025 discloses an electrical circuit system fixed on a fabric article, as illustrated in the description. To fix a circuit onto a fabric article, such is garment is complicated and it increases the weight and thickness of the garment. It is not ergonomic, nor is it environment friendly.

4. The membrane switch disclosed in U.S. Pat. No. 6,600,120 is similar to the prior art shown above. Because the upper and low conductors are the same, it needs multiple terminals to connect with processor 002.

5. The textile switching device disclosed in U.S. Pat. No. 7,145,432 also needs multiple output transmission wires, which make it complicated.

6. U.S. Pat. No. 6,642,467 discloses an electrical switch, in which the upper and lower conductors are only textile switch or pressure sensor, and it needs three components.

7. U.S. Pat. No. 6,714,117 discloses a position sensor, which is comprised of two conductive layers and a mid layer in between to detect the signal variations caused by applied force. It is very complicated.

8. U.S. Pat. No. 6,493,933 discloses a textile circuit, in which each electronic component has its own transmission line. Furthermore, components such as processors, IC, Bluetooth, batteries are not water-proof or washable and they produce electromagnetic waves.

9. U.S. Pat. No. 6,809,662 discloses a system with multiple pressure sensors in which conductors are coated on both sides of a polymer film as electrodes. However, transducers are needed to detect the variations of capacitance or resistance at the pressed positions. If one part of the film is broken, the whole system would fail.

The above-mentioned prior art designs need more steps during operations. For example, the user has to connect four sets of terminals if the sensing apparatus has four outputs to signal processor. The designs in these prior patents involve complicated components or too many wires. They are not washable or too difficult to manufacture. It is also difficult to repair once it fails, because it is difficult to find out the locations and the reasons.

Thus, it can be seen that there still exist inconvenience and shortcomings in the structures and applications of current sensors wirings. These would need further improvements. To overcome the problems associated with sensor apparatus wirings, manufacturers are eagerly looking for solutions. However, it has been some time and no suitable designs have been developed. The products available out there do not have the proper structures for solving these problems. This is apparently an urgent problem to be solved in this field. Therefore, how to develop a novel sensing apparatus that is low cost, easy to operate and manufacture, is an important topic for the research and development, and an important goal of the industry.

DESCRIPTION OF THE INVENTION

The present invention aims to overcome some of the shortcomings of the prior art sensing apparatus and to provide sensing apparatus with novel structures. The technical problems addressed by the present invention includes decreasing the number of terminals such that it would be easy to operate an would not be prone to short circuits.

The objectives of the present invention and the technical problems are solved with the following technical solutions. In accordance with embodiments of the invention, a sensing apparatus is comprised of a base layer and a plurality of sensors disposed on the base layer. The plurality of sensors form a circuit with two output terminals. The two output terminals produce a "circuit output," which varies according to the forces applied on the sensors. Each sensor has a unique "sensor output," which is different from any other sensor. Any sensor or a combination of more than one sensor gives a sum "circuit output" value that is different from a value of any other individual sensors or any other combinations of sensors.

In addition, an objective of the present invention and solutions to the technical problems can also be implemented with the following approaches:

An above-described sensing apparatus may include a signal processor connected to the two terminals. The signal processor senses and detects the "circuit output" value.

In an above-described sensing apparatus, a signal processor can sense and detect where the output sensor is located on the base layer.

In an above-described sensing apparatus, the base layer may be made of textile or leather.

In an above-described sensing apparatus, the sensors include pressure sensors, tension sensors, photo sensors, or temperature sensors.

An above-described sensing apparatus may also include a two-sectioned switch on a cloth base layer.

An above-described sensing apparatus may comprise a pressure sensor or a strain gauge.

In an above-described sensing apparatus, a sensor includes a first sensing area disposed on the base layer; an accessory disposed on the base layer correspondent to the first sensing area; a second sensing area disposed on the accessory and also correspondent to the first sensing area; and an electronic component electrically connected to the first or second sensing area.

In an above-described sensing apparatus, said electronic component may be a resistor, an inductor, or a capacitor.

In an above-described sensing apparatus, said sensor may include a light-emitted-diode (LED) electrically connected to the first or second sensing area.

The objectives of the present invention and solutions to the technical problem can be implemented using the following approaches: according to embodiments of the invention provide a bed sheet, a garment, a seat, a vehicle that includes the sensing apparatus described above.

The objectives of the present invention and solutions to the technical problems can be implemented as follows: according to embodiments of the invention, a physiological function detecting system for detecting a physiological function of a user is provided. The system comprises a sensing apparatus described above, which senses the posture changes of the user's body and responds the posture changes by generating a circuit output; at least one detector to detect physiological functions based on a trigger signal and to generate a corresponding signal; and a signal processor that connects to the sensing apparatus and the detector, to receive the circuit outputs and the signals, and to send a trigger signal, according to a first criterion, to trigger the at least one detector to detect the physiological functions.

The objectives of the present invention and solutions to the technical problems can also be implemented as follows: according to embodiments of the invention, a physiological function detecting system is provided for detecting a physiological function of a user. The system comprises an above-described sensing apparatus, which senses changes in the user's body posture and, in response to the posture changes, sends a circuit output; at least one therapy device; the sensing apparatus senses physiological functions based on a trigger signal and generates a signal; and a signal processor that connects to the sensing apparatus and the therapy device. The signal processor is to receive the circuit output and the signal of the sensing apparatus, and to selectively send the trigger signal based on a first criterion to initiate the at least one therapy device. The therapy device can be a heater, a transcutaneous electrical nerve stimulator (TENS), an ultrasonic device, or an electrical shock device.

Objectives of present invention and solution to the technical problems can be implemented as follows: according to embodiments of the invention, a sensing apparatus is provided, which comprises at least one first layer containing at least one first sensing area; at least one accessory, made of Velcro®, containing at least one second sensing area at a location corresponding to a location of the first sensing area on the first layer. A Velcro® is provided on a clothing material corresponding to the accessory to allow attachment of the accessory. The first sensing area is coupled to the second sensing area, and the coupling state changes depending on an applied force.

In the above sensing apparatus, to conductive circuit on the accessory is comprised of a conductive Velcro®.

In the above sensing apparatus, the accessory is surrounded by a coil, and the first sensing area or the second sensing area is made of a magnetic material such that a current is induced in the coil with changes in the applied force.

Objectives of the present invention and solution to the technical problem can also be implemented as follows: according to embodiments of the invention, a sensing apparatus is provided, which comprises a textile layer containing at least one crevice surrounded by a coil; and an inductance sensor area comprising a first sensing area and a second sensing area disposed on both sides of the crevice. The first sensing area and the second sensing area comprise a magnetic material. The shapes of the crevice and the inductance sensor area change according to the applied force, and changes in the applied force induce a current in the coil.

Objectives of the present invention and solution to the technical problem can also be implemented as follows: according to embodiments of the invention, a sensing apparatus is provided, which comprises at least one first layer having at least a first sensing area; at least an extended part having at least one accessory; and at least one connector connected to the accessory. At least a second sensing area is disposed on the extended part at a location correspondent to the first sensing area, wherein the first and the second sensing areas are inductively coupled (connected), the inductive state changes with the applied force. The accessory is surrounded by a coil and the first and the second sensing areas comprise a magnetic material such that a current is induced in the coil when the applied force changes.

Compared with current art, the present invention has obvious advantages and benefits. As shown in the above description, sensing apparatus of the present invention have substantial improvements and utility such that they can be widely applied in the industry. Their advantages include at least the following:

1. Sensing apparatus of the invention have fewer transmission wires. They are easy to operate by the user and are less prone to having short circuits 2. Sensing apparatus of the invention have can be applied to fabric, leather, apparel, bed sheets, and seats. They have fewer connectors so that a user feel more comfortable;

3. Sensing apparatus of the invention can readily detect a location of a mal-functioning sensor such that it is easy to repair and replace.

The above description is only a summary of embodiments of the invention. In order to facilitate better understanding of embodiments of the present invention such that one can follow the description to practice the invention, as well as to make embodiments of the invention and their objectives, characteristics and advantages easier to understand, the following sections use examples, together with drawings, to explain in more details.

BRIEF DESCRIPTION OF THE DRAWINGS

FIG. 12 shows a shematic diagram of the eighth preferred embodiment of the present invention;

FIG. 13 shows a shematic diagram of the ninth preferred embodiment of the present invention;

FIG. 14 shows a shematic diagram of the tenth preferred embodiment of the present invention;

FIG. 15 shows a shematic diagram of the eleventh preferred embodiment of the present invention;

FIG. 16 shows a shematic diagram of the twelfth preferred embodiment of the present invention;

THE PREFERRED EMBODIMENTS

To further illustrate embodiments of the invention and their objectives and benefits, the following description, using drawings and examples, explains in detail sensing apparatus of the invention, their applications, structure, characteristics, and functions.

Sensing apparatus of the present invention each comprise a base layer and a plurality of sensors. The plurality of sensors are disposed on the base layer and electrically connected to form a circuit with two output terminals. The two output terminals give a "circuit output" value that varies with the forces applied on the sensors. Each sensor has its unique "sensor output" value that is different for different sensors. A lump sum of sensor output value of any one or more sensors is different from any other sensor output values of another one or more combination of sensors. The form of the "sensor output" values can be resistance, capacitance, or inductance. The said sensor can be pressure sensors or strain gauges.

In one of the preferred embodiments, the present invention may contain two sensors.

A sensing apparatus of the invention may also include a signal processor that connects to the two output terminals for detecting the "circuit output" values and sends a signal about the location of the sensor that experiences the applied force. The "circuit output" value is unique for each sensor. Therefore, the sensing apparatus has the ability to identify the location of a sensor.

The following, using examples, further explains the invention.

The First Preferred Embodiment

Figure 5:
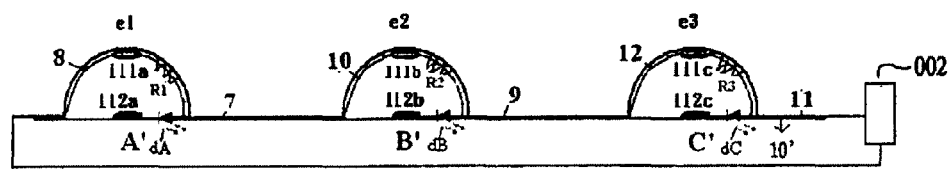
FIG. 5 shows a shematic diagram of the first preferred embodiment of the present invention.

Referring to FIG. 5, which shows a sensing apparatus of the invention. A sensing apparatus of this example includes a textile layer 10' and sensors A', B', and C'. The sensors A', B', and C' are disposed on the textile layer 10' and electrically connected.

Sensor A' comprises a sensing area 112a, an accessory e1, and two output terminals 7, 8, wherein the sensing area 112a is disposed on the textile layer 10', and the accessory e1 is disposed above the textile layer 10' at a location corresponding to the location of sensing area 112a. The accessory e1 includes a sensing area 111a, one end of which is connected to a 100Ω resistor R1. The accessory e1 has a hemisphere shape. The output terminal 7 is connected to both the sensing area 112a and the resistor R1, and the output terminal 8 is connected to the other end of the sensing area 111a. The accessory e1 is flexible. The sensing areas 111a and 112a touch each other when pressed to short circuit the resistor R1. When the applied force is removed, the sensing areas 111a and 112a will return to the original shape/configuration.

Sensor B' comprises a sensing area 112b, an accessory e2, and two output terminals 9, 10. The structure of sensor B' is same as that of sensor A', while the resistor R2 is 300Ω. Its output terminal 10 is connected to output terminal 7 of sensor A'.

Sensor C' comprises a sensing area 112C, an accessory e3, and two output terminals 11, 12. The structure of sensor B' is same as that of A', while the resistor R2 is 500Ω. Its output terminal 12 is connected to output terminal 9 of sensor B'.

Sensor A', B', and C' are electrically connected to form a circuit with output terminals 8 and 11.

In this example, the sensing apparatus also includes a signal processor 002 that electrically connects with output terminals 8 and 11.

In this example, processor 002 comprises a device to measures the resistance. It needs only two wires and two terminals, very economical in the use of materials.

In this sensing apparatus example, when no external force is applied to the sensors A', B', and C', the resistance measured by the signal processor 002, i.e., the "circuit output", is 900Ω. When only sensor A' is pressed, the circuit output detected by the processor 002 is 800Ω. When only sensor B' is pressed, the circuit output detected by the processor 002 is 600Ω. When only sensor C' is pressed, the circuit output detected by the processor 002 is 400Ω. When both sensor A' and B' are pressed, the circuit output detected by the processor 002 is 500Ω. When both sensor A' and C' are pressed, the circuit output detected by the processor 002 is 300Ω. When both sensor B' and C' are pressed, the circuit output detected by the processor 002 is 100Ω. When all sensors are pressed, the circuit output detected by the processor 002 is 0Ω. That is, the output values detected by the processor are different in all these situations. Each circuit output of any one or any combinations of sensors under pressure is different from that of any other one or other combinations of sensors.

When this embodiment is applied in socks or shoes, the signal processor 002 needs only two terminals to detect changes in three pressure points for the analysis of the right foot or left foot walking status of a user. For example, it can identify whether the user fell or not by determining whether none of the sensors are pressed.

This sensing apparatus example can also includes an LED. As shown in FIG. 5, an LED dA is placed between the sensing area 112a and the output terminal 7. Because it has LED dA, when a sensor (e.g., sensor A') is pressed, it will light up. If it won't light up, it would indicate that the sensor at this location has a problem. Therefore, addition of LED makes it more fun and can also help indicate whether a sensor has any. This example can also be applied in a keyboard.

The Second Preferred Embodiment

Figure 6:
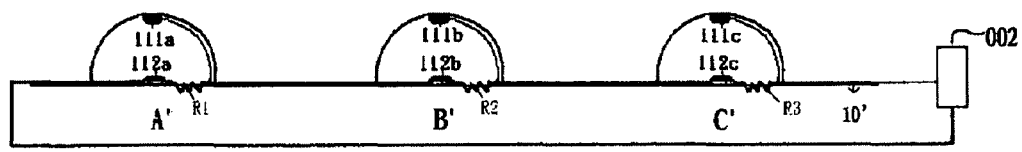
FIG. 6 shows a shematic diagram of the second preferred embodiment of the present invention.

Referring to FIG. 6, which shows a second exemplary embodiment of the invention.

This second example is similar to the first, but the resistors are placed above the sensing areas on the base layer, and no LED is installed.

Figure 1:
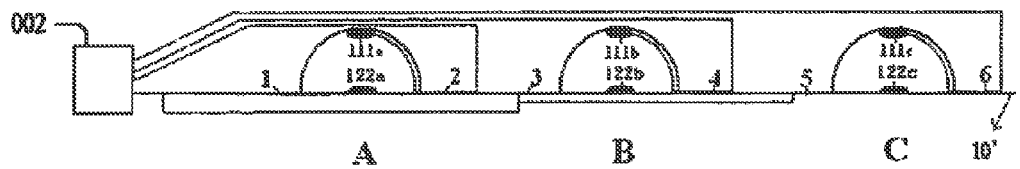
FIG. 1 shows a side view shematic diagram of a current sensing apparatus.
Figure 2:
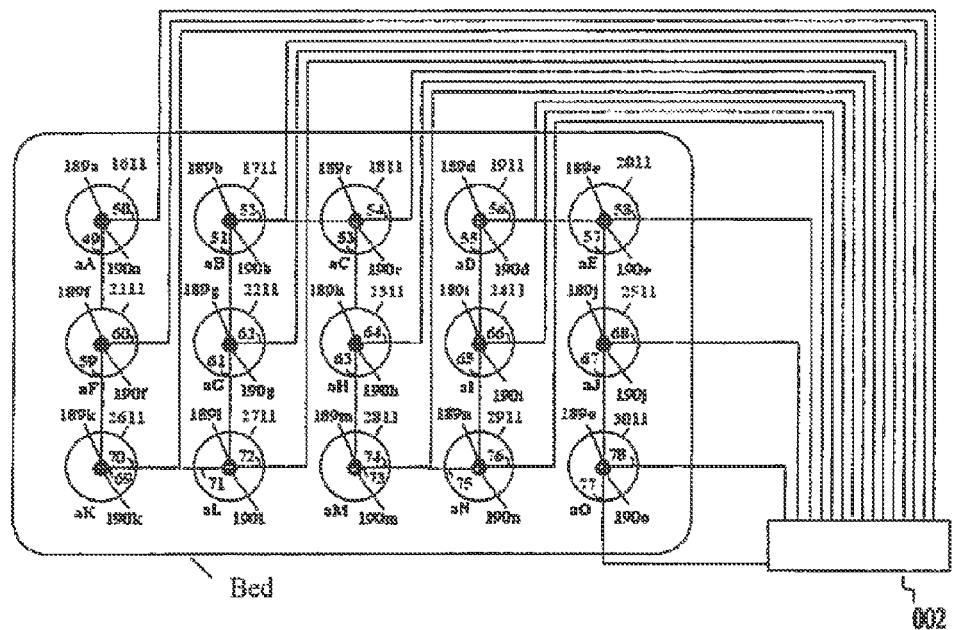
FIG. 2 shows a shematic diagram of a prior art sensing apparatus applied in a bed sheet or a seat cushion.
Figure 3:
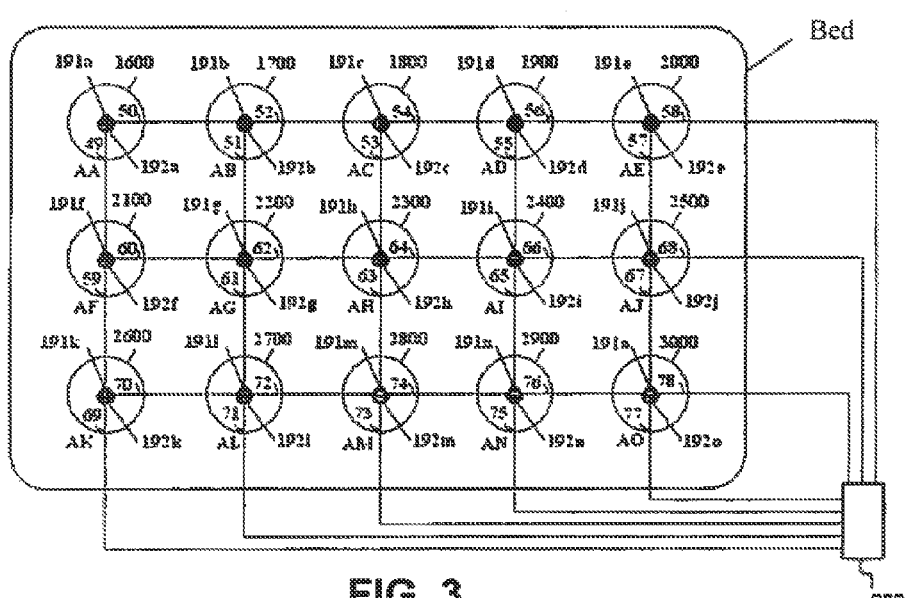
FIG. 3 shows a schematic diagram of another prior art sensing apparatus applied in a bed sheet.
Figure 4:
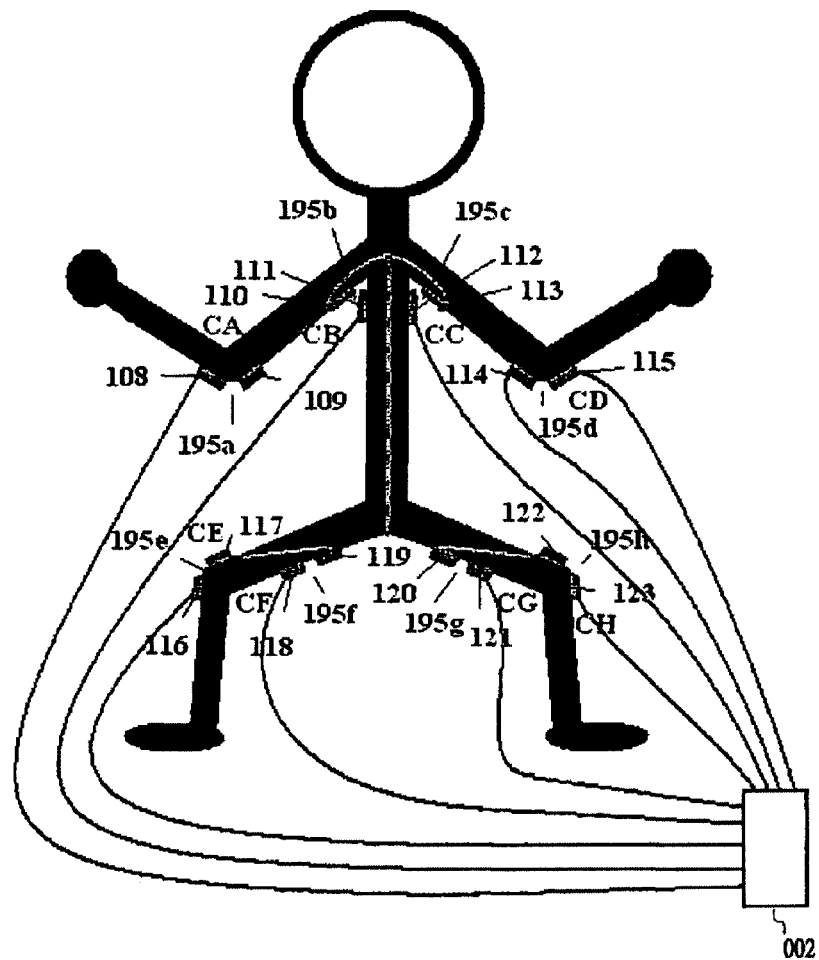
FIG. 4 shows a shematic diagram of a prior art sensing apparatus applied on a garment.

In the above two examples, the resistance values detected by the signal processor 002 is sufficient to identify the changing conditions of sensors A', B' and C', and this is very efficient because the signal processor 002 uses only two input terminals to read one signal, and therefore the signal processor 002 can have spare terminals for receiving other signals. In contrast, the structure shown in FIG. 1 would request four terminals to read three signals.

The Third Preferred Embodiment

Figure 7:
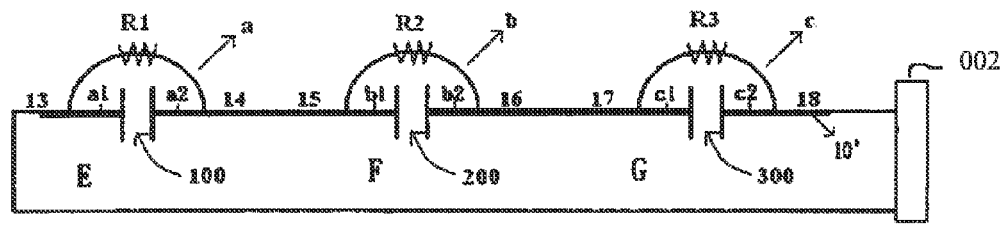
FIG. 7 shows a shematic diagram of the third preferred embodiment of the present invention.

Referring to FIG. 7, which shows a schematic of a third exemplary embodiment. A sensing apparatus according to this third example comprises a cloth layer 10' and sensors E, F, and G.

In the cloth layer 10', there are three crevices 100, 200, and 300. The sensors E, F, G are strain gauges and are placed near crevices 100, 200, and 300.

The sensor E comprises two inductive sensing areas a1 and a2 on both sides of the crevice 100, an accessory a, and two output terminals 13 and 14. The accessory a may be a conductive material and is connected to the sensing areas a1 and a2 located at two ends of the crevice 100. In addition, the accessory is equipped with a 100Ω resistor R1. In the absence of applied force, the resistance of to the sensor E is zero. When a force is applied to pull the crevice 100 apart and separate the sensing areas a1 and a2, the resistance of the sensor E becomes that of the resistor R1, 100Ω.

The structures of the sensors E, F and G are basically the same, but their resistors are 100Ω, 300Ω, and 500Ω, respectively.

The above-described sensors E, F, and G are electrically connected to form a circuit with output terminals 13 and 18. Between the output terminal 13 and output terminal 18, there is an inductance value.

In this example, the sensing apparatus further includes a processor 002, which is connected with the output terminals 13 and 18.

In this example, the signal processor 002 includes a resistance sensor for detecting a resistance of the circuit. The processor 002 needs only two terminals and two transmission wires, very economical in using materials.

In this example sensing apparatus, when sensors E, F, and G are not subjected to any external force, the resistance detected by the processor 002 is 0. When strain sensor E is under an external force that pulls crevice 100 open, the resistance detected by the processor 002 is close to 100Ω. When strain sensor F is under an external force that pulls crevice 200 open, the resistance detected by the processor 002 is close to 300Ω. When strain sensor G is under an external force that pulls crevice 300 open, the resistance detected by the processor 002 is close to 500Ω. When strain sensors E, F are under an external force that pulls crevices 100 and 200 open, the resistance detected by the processor 002 is close to 400Ω. When strain sensors E, G are under an external force that pulls crevices 100 and 300 open, the resistance detected by the processor 002 is close to 600Ω. When strain sensors F, G are under an external force that pulls crevices 200 and 300 open, the resistance detected by the processor 002 is close to 800Ω. When strain sensors E, F, G are under an external force that pulls crevices 100, 200, and 300 open, the resistance detected by the processor 002 is close to 900Ω. That is, the resistance values produced by these sensors are different. Any sensor value sum produced by one or more sensors is different from a value produced by any other one or more sensors.

In addition, the accessories a, b, c are also protective devices to prevent the structures of the strain sensors form being destroyed by excessive force. For example, assuming the threshold of the sensor E is 500 grams, and under a force greater than 100 grams, the crevice 100 may be torn or acquire prematurely elastic fatigue. With accessory a, with a force greater than 500 grams, the crevice is open and the accessory a is also stretched. Therefore, excess force would not affect crevice 100. That is, crevice 100 will not be subjected to an external force greater than 1000 grams. In addition, when the tension force is too large, accessories a, b, c would break first. The signal processor 002 can detect such breakage. For example, if accessory a breaks, under the serial connection configuration, when crevice 100 is open, the obtained resistance value would be very large. In this case, a new accessory a can be sew back on, without having to replacing the entire sensor E. The process is easy and environmentally friendly, saves resources, and is easy to repair.

The Fourth Preferred Embodiment

Figure 8:
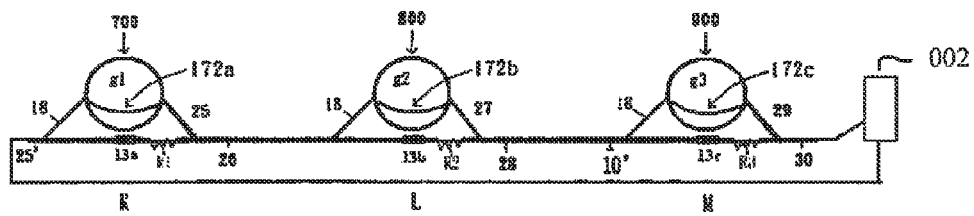
FIG. 8 shows a shematic diagram of the fourth preferred embodiment of the present invention.

Referring to FIG. 8, which shows a sensing apparatus of a fourth preferred embodiment of the invention. This sensing apparatus comprises a cloth base layer 10' and sensors K, L, and M. These sensors K, L, M are disposed on the base layer 10' and electrically connected.

The sensor K comprises a sensing area 13a, an accessory 700, and two output terminals 25 and 26. The sensing area 13a is disposed on the base layer 10', and serially connected to a resistor R1 with the two output terminals 25 and 26. The accessory 700 is disposed above the base layer 10' at a location correspondent to the sensing area 13a. The accessory includes an elastic sphere g1, which is fixed onto the base layer 10' by two connectors 18; and a sensing area 172a that spans from the elastic sphere g1 to the output terminals 26. the accessory g1 is elastic. The sensing area 13a and sensing area 172a contact each other under an applied force to cause a short circuit of the resistor R1; they return to the original shape once the pressing force disappear.

The sensor L comprises a sensing area 13b, an accessory 800, and two output terminals 27 and 28. The structure of sensor L is similar to that of sensor K, but the resistor R2 has a resistance of 300Ω. Output terminal 27 is connected to output terminal 26.

The sensor M includes a sensing area 13c, an accessory 900 and two output terminals 29,30. The structure of sensor M is similar to that of sensor L, but the resistance of resistor R3 is 500Ω. Output terminal 29 is connected to output terminal 28.

The sensors K, L, and M are electrically connected to form a circuit with output terminals 25' and 30.

In this example, the sensing apparatus further includes a processor 002, which is electrically connected with output terminal 25' and output terminal 30.

With a sensing apparatus of this example, when sensors K, L, and M are not pressed by an external force, the resistance detected by the processor 002 is 900Ω. When sensor K is pressed, sensing areas 13a and 172a touch to short circuit the R1, and the resistance detected by the processor 002 is 800Ω. When sensor L is pressed, the resistance detected by the processor 002 600Ω. When sensor M is pressed, the resistance detected by the processor 002 400Ω. When sensor L and sensor M are pressed, the resistance detected by the processor 002 100Ω. When sensor K and sensor M are pressed, the resistance detected by the processor 002 300Ω. When sensor K and sensor L are pressed, the resistance detected by the processor 002 500Ω. When sensors K, L, and M are pressed, the resistance detected by the processor 002 0Ω. That is, the detected values are all different. The sum value of any one or more sensors is different from that of any other sensor or other combination of sensors.

The Fifth Preferred Embodiment

Figure 9:
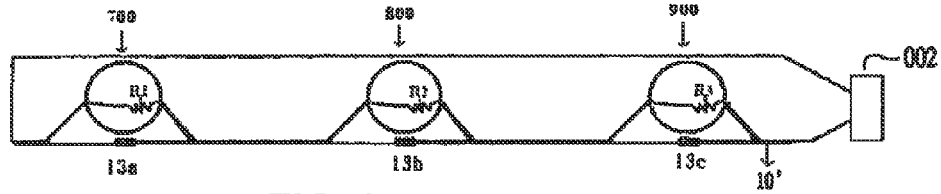
FIG. 9 shows a shematic diagram of the fifth preferred embodiment of the present invention.

Referring to FIG. 9, which shows a fifth preferred embodiment of the invention. Compared with example 4, the resistors in a sensing apparatus of this embodiment are disposed on the accessories, and the output terminals of the sensors are connected to the two ends in the sensing areas on the accessories.

In this embodiment, all the resistance values should be different and no sum or difference of any arbitrary combination of the resistors would produce the same value, to prevent the processor 002 from making an incorrect identification. For example, the resistances can be proportional to a geometric series with a ratio of 1, 2, 4, 8, 16, 32, and 64 to ensure that no sum of two or more of these numbers would be the same. Of course, one can also use values of a combination of three different magnitudes, e.g., 1Ω, 10Ω, 100Ω. Then, any sensor will not produce a same result. Of course, the above-described approaches are not the only ways to ensure that the resistance values would be different.

Here is one example wherein wrong resistance vales are selected. Assuming the resistance of the sensor 13a is 100Ω, the resistance of the sensor 13b is 200Ω, the resistance of the sensor 13 is 300Ω, then the circuit output of resistors 13a and 13b is 300Ω, the same values as resistor 13c. With this circuit output, the signal processor 002 cannot determine whether sensors 1 and 2 are pressed or only sensor 3 is pressed.

The Sixth Preferred Embodiment

Figure 10:
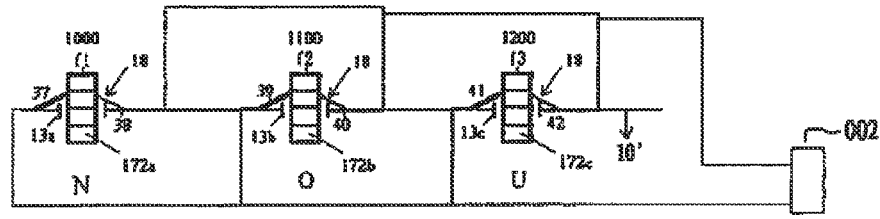
FIG. 10 shows a shematic diagram of the sixth preferred embodiment of the present invention.

Referring to FIG. 10, which shows a sixth preferred embodiment of the invention. This sensing apparatus comprises a cloth base layer 10' and sensors N, O, and U.

The sensors N, O, U are disposed on the base layer 10' and electrically connected.

The sensor N comprises a sensing area 13a, an accessory 1000, and two output terminals 37 and 38. The sensing area 13a is disposed on both sides of an opening in the base layer 10'. The accessory 1000 is disposed above the base layer 10' at a location correspondent to the sensing area 13a. The accessory 1000 comprises a column f1. The column f1 is fixed on the cloth base layer 10' by two connectors 18, and a sensing area 172a on the column f1. The sensing area 172a comprises three sensing areas with different resistances, which are 100Ω, 300Ω, 500Ω, respectively. All three different resistors are connected to output terminal 37. The column f1 penetrates the opening in the base layer 10' and contacts the sensing area 13*a* on both sides of the opening. The output terminal 38 is electrically connected to the sensing area 13*a*. When an external force is applied to the accessory 1000, it moves up or down to give a displacement relative to the base layer 10 to produce 100Ω, 300Ω, or 500Ω, three different resistance values.

The structures of sensors O and U are the same as that of the sensor N, but the resistors on column f2 are 1000Ω, 3000Ω, and 5000Ω, and the resistors on column f3 are 10000Ω, 30000Ω, and 50000Ω.

The sensors N, O, and U are electrically connected to form a circuit with the output terminals 37 and 42.

The sensing apparatus in this embodiment also includes a signal processor 002 to electrically connect to the output terminals 37 and 42.

With a sensing apparatus of this example, an external force is applied to press a sensor N, O, or U, or to pull the base layer 10' to give an up-and-down relative displacement. Thus, the signal processor 002 can detect the changes in resistance and identify the sensor that produces the resistance change.

The Seventh Preferred Embodiment

Figure 11:
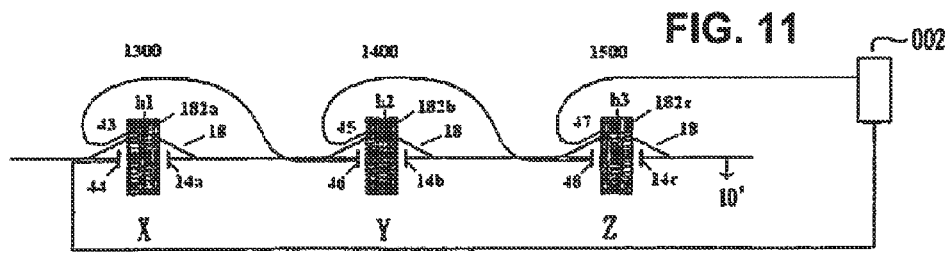
FIG. 11 shows a shematic diagram of the seventh preferred embodiment of the present invention.

Referring to FIG. 11, which shows a seventh preferred embodiment. This sensing apparatus comprises a base layer 10' and sensors X, Y, and Z.

The sensors X, Y, and Z are disposed on the base layer 10' and electrically connected.

The sensor X is connected to give analog outputs. The accessory 1300 of the sensor X comprises a column h1, two connecting parts 18 fixed on the cloth base layer, wherein column h1 has a sensing area 182*a* made of a variable resistor with resistance ranging from 1000Ω to 2000Ω, and an output terminal 43. The sensor X's accessory (column h1) penetrates an opening in the base layer 10'. A first sensing area 14*a*, having a resistance of 0, is located at the opening. The sensing area 14*a* directly contacts accessory 1300 and connects with output terminal 44. The accessory 1400 of the sensor Y comprises a column h2, two connecting parts 18 fixed on the cloth base layer. A sensing area 182*b* on column h2 comprises a variable resistor with resistance ranging from 2100Ω to 4000Ω, connected to an output terminal 45. The sensor Y's accessory (column h2) penetrates an opening in the base layer 10'. A first sensing area 14*b* is located at the opening and has a resistance of about 0. The sensing area 14*b* directly contacts the accessory 1400 and connects with an output terminal 46. The accessory 1500 of the sensor Z comprises a column h3, two connecting parts 18 fixed on the cloth base layer. The column h3 has a sensing area 182*c*, which is a variable resistor with resistance ranging from 6100Ω to 8000Ω, connected to an output terminal 47. The accessory 1500 of sensor Z penetrates an opening in the base layer 10'. A first sensing area 14*c* is disposed at the opening, which has a resistance of about 0. The sensing area 14*c* directly contacts the accessory 1500 and connects with output terminal 48. Every accessory 1300, 1400 or 1500 uses connecting parts 18 to connect with the base layer such that the accessories are fixed on the cloth base layer and their output terminals 43, 45, 47 are connected to the cloth base layer 10' via the connecting parts 18.

The output terminal 43 of the sensor X is electrically connected to the output terminal 46 of the sensor Y. The output terminal 45 of the sensor Y is electrically connected to the output terminal 48 of the sensor Z. The output terminal 44 of the sensor X and the output terminal 47 of the sensor Z are separately connected to the two input terminals of the signal processor 002, for form a serial connection. Thus, the resistance variation caused by applied forces can be measured by the signal processor 002 via the two input terminals.

The Eighth Preferred Embodiment

Referring to FIG. 12, which shows an eighth preferred embodiment of the invention. This sensing apparatus comprises a base layer 10', and sensors HA, HB, and HC.

The sensors HA, HB, and H C are disposed on the base layer 10' and electrically connected.

The accessory 400 of the sensor HA includes a sensing area 201*a*. The accessories 400, 500. and 600 are separately fixed on the cloth base layer 10'. On the base layer, at a location corresponding to the location of sensing area 201*a*, are placed two open circuit points 200*a* and 200*b*, connected by a 100Ω resistor R1. The two open circuit points 200*a* and 200*b* are connected to terminals 166 and 167. The accessory 500 of the sensor HB includes a sensing area 201*b*. The accessories 400, 500, and 600 are separately fixed on the cloth base layer 10'. On the base layer, at a location corresponding to the location of the sensing area 201*b*, are placed two open circuit points 210*a* and 210*b*, connected by a 300Ω resistor R1. The two open circuit points 210*a* and 210*b* are connected to terminals 168 and 169. The accessory 600 of the sensor HC includes a sensing area 201*c*. The accessories 400, 500, and 600 are separately fixed on the cloth base layer 10'. On the base layer, at a location corresponding to the location of the sensing area 201*c*, are placed two open circuit points 220*a* and 220*b*, connected by a 500Ω resistor R1. The two open circuit points 220*a* and 220*b* are connected to terminals 170 and 171. The accessories have a cap shape and are made of plastic, latex rubber, silicone rubber, synthesized sponge or other elastic material. They would change shapes under an applied force and will return to their original shapes when the external force is removed. The output terminal 166 is connected to the processor 002. The terminal 167 is connected to the terminal 168, so is 169 and 170. The terminal 171 is connected to the other terminal of the signal processor 002 to form a circuit. When no external force is applied, the resistance of this circuit is 900Ω. When only the sensor HA is pressed, the sensing area 201*a* contacts the two open circuit points 200*a*, 200*b* on the base layer to form a short circuit. The resistance for the entire circuit becomes 800Ω. When the external force is removed, the open circuit points 200*a*, 200*b* become open circuit again, and the resistance of the entire circuit returns to 900Ω. The same analysis applies to sensors HB and HC.

The Ninth Preferred Embodiment

Referring to FIG. 13, which shows a ninth preferred embodiment i of the invention. This sensing apparatus comprises a base layer 10', and sensors ZA, ZB, and ZC.

The operating principle of the pressure sensors ZA, ZB, ZC is the same as that of the eighth example, but the sensing areas 201*a*, 201*b*, and 201*c* of the accessories 400, 500, and 600 can directly touch the both ends of the resistors R1, R2, and R3 to short circuit 300*a* and 300*b*, 310*a* and 310*b*, or 320*a* and 320*b*, when the sensor is pressed.

The Tenth Preferred Embodiment

Referring to FIG. 14, which shows a tenth preferred embodiment of the invention. this sensing apparatus comprises a base layer 10', and sensors KA, KB, and KC.

The sensors KA, KB, and KC are connected in parallel to the signal processor 002 by two output transmission wires 178 and 184. The accessory 400' includes two insulator layers L1 and L2 fixed on the base layer 10' connected by a connector 18. On the connector 18, there is a sensing area 301a having a 1 KΩ resistor. The accessory 500' includes two insulator layers L1 and L2 fixed on the base layer 10' and connected by a connector 18. On the connector 18, there is a sensing area 301b having a 2 KΩ resistor. The accessory 600' includes two insulator layers L1 and L2 fixed on the base layer 10' and connected by a connector 18. On the connector 18, there is a sensing area 301c having a 4 KΩ resistor. Correspondent to the location of the sensing area 301a, two open circuit points 70a and 70b are placed, which are connected by two output transmission wires 178 and 179. Correspondent to the location of the sensing area 301b, two open circuit points 80a and 80b are placed, which are connected by two output transmission wires 181 and 182. Correspondent to the location of the sensing area 301c, two open circuit points 90a and 90b are placed, which are connected by two output transmission wires 183 and 184. The output transmission wires 178, 181, and 183 are connector together to the signal processor 002. The output transmission wires 179, 182, and 184 are also connected together and then connected to the other terminal of the signal processor 002. When no external force is applied, the resistance is infinite. When only sensor KA is pressed by an external force, the sensing area 301a touches both open circuit points 70a and 70b. The resistance of the resulting circuit becomes 1 kΩ. When the external force is removed, the sensor returns to its original shape and the resistance of the circuit becomes infinite again. The same analysis applies to sensors KB and KC.

In addition, in the structure of FIG. 14, resistor R1 can be connected directly to the open circuit points 70a and 70b. Resistor R2 can be directly connected to the open circuit points 80a and 80b. Resistor R3 can be directly connected to the open circuit points 90a and 90b. At the same time, the resistances of the sensing area on the connector 18 should be change to zero. The circuit will give same effects as that shown in FIG. 14, except that the resistors are now on the base layer.

In such a configuration, R1 can be a thermistor to allow the processor 002 to measure the outside or body temperature changes. If the outside temperature is very low, the signal processor can initiate a heater to keep the user warm. When the sensor KA is pressed, the signal processor can measure the resistance change at the pressed location to infer the body temperature change. Therefore, the sensor KA is not only a pressure sensor, but also a thermometer.

By the same token, R1 can also be a photo resistor or color sensor which can reflect the intensity or color of incident light by its resistance. When pressed, the signal processor 002 can determine whether the light is on or off, blue or red, and responds accordingly. For example, when the light is off, the signal processor 002 can turn on the LED or optic fibers on a cloth. When light transmission sensor detects different lights, the signal processor 002 can produce different response, allowing the color or strength of a cloth material to change with the environment. Thus, the sensor is not only a pressure sensor but also a photo or color sensor.

As describe in the eighth embodiment, the accessory can be an arch-shaped structure, and be made of plastic, latex rubber, silicone rubber, synthesized sponge or other elastic materials, wherein a sensing area made of a conductive material (such as a conductive silicone) is designed to contact the two open circuit points on the base layer. The sensors can be connected in parallel to two output wires to the signal processor 002.

There is a common feature in the eighth, ninth, and tenth preferred embodiments (examples), i.e., no output terminals, but sensing areas, are disposed on the accessories. All circuits are on the base layer 10', which makes it easier to manufacture, using fewer wires, and more environmentally friendly.

The Eleventh Preferred Embodiment

Referring to FIG. 15, which shows an eleventh preferred embodiment of the invention. This sensing apparatus comprises a base layer 10', and sensors W1, W2, and W3.

The sensors W1, W2, and W3 are disposed on the base layer 10' and electrically connected.

The accessory 666 of the sensor W1 includes a sensing area 666a. Corresponding to the location of accessory 666a, two sensing areas 666b and 666c are disposed on the base layer 10', and a piece of dielectric material is placed between sensing areas 666b and 666c to form a 10 pF capacitor C1. The accessory 667 of the sensor W2 includes a sensing area 667a. Corresponding to the location of accessory 667a, two sensing areas 667b and 676c are disposed on the base layer 10', and a piece of dielectric material is placed between sensing areas 667b and 667c to form a 20 pF capacitor C2. The accessory 668 of the sensor W3 includes a sensing area 668a. Corresponding to the location of accessory 668a, two sensing areas 668b and 668c are disposed on the base layer 10', and a piece of dielectric material is placed between sensing areas 668b and 668c to form a 100 pF capacitor C3. One terminal of capacitor C1, i.e., the sensing area 666b, is connected with a transmission wire 771, and the other terminal of capacitor C1, i.e., sensing area 666c, is connected with a transmission wire 772. One terminal of capacitor C2, i.e., the sensing area 667b, is connected with a transmission wire 773, and the other terminal of capacitor C2, i.e., sensing area 667c, is connected with a transmission wire 774. One terminal of capacitor C3, i.e., the sensing area 668b, is connected with a transmission wire 775, and the other terminal of capacitor C3, i.e., sensing area 666c, is connected with a transmission wire 776.

The transmission wires 771, 773, and 775 are connected together as one terminal to the signal processor 002, and the transmission wires 772, 774, and 776 are also connected together as another terminal to the signal processor 002. When only sensor W1 is pressed, the sensing area 666a touches both ends of capacitor C1 to short circuit the capacitor C1, thereby the capacitance detected by the signal processor 002 changes from 130 pF (which is the value when no external force is applied) to 120 pF. When only sensor W2 is pressed, the sensing area 667a touches both ends of capacitor C2 to short circuit the capacitor C2, thereby the capacitance detected by the processor 002 changes from 130 pF to 110 pF. When only sensor W3 is pressed, the sensing area 668a touches both ends of capacitor C3 to short circuit the capacitor C3, thereby the capacitance detected by the processor 002 changes from 130 pF to 30 pF. When both sensors W2 and W3 are pressed, the value detected by the processor 002 is 100 pF. When both sensors W1 and W3 are pressed, the value detected by the processor 002 is 20 pF. When all three sensors are pressed, the value detected by the processor 002 is 0 pF. Thus, the sensing apparatus can detect the body movement of a user.

The Twelfth Preferred Embodiment

The sensor of this embodiment can use capacitors. As shown in FIG. 16, a sensing apparatus according to twelfth embodiment of the invention comprises a base layer 10' and sensors Q1, Q2, and Q3.

The sensors Q1, Q2, and Q3 are disposed on the base layer 10' and electrically connected.

The capacitance between two conductor plates is $C = \in A/d$, wherein $\in$ is the dielectric constant. Using materials of different dielectric constants, different areas A, and different distance d between the conductor plates, one can design capacitors with different capacitance values.

Figure 17:
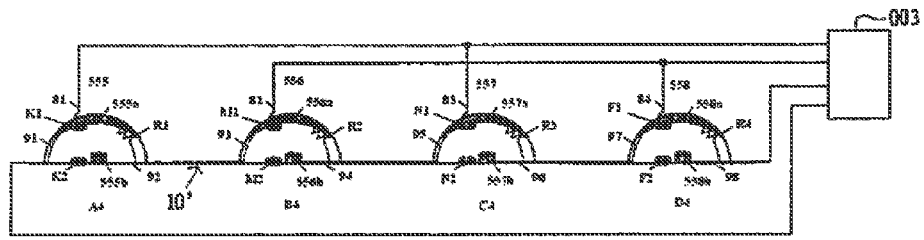
FIG. 17 shows a shematic diagram of the preferred embodiment of the physiological function signal detecting system by the present invention.

As shown in FIG. 17, the accessory 333 of the sensor Q1 includes a sensing area 333a with an area A1, under which a dielectric material with dielectric constant c1 is disposed. At a location corresponding to the location of sensing area 333a on the base layer 10', there is another sensing area 333b with area A1. A distance between the two sensing areas 333a and 333b is d1. Likewise, the accessory 334 of the sensor Q2 includes a sensing area 334a with an area A2, under which a dielectric material with dielectric constant ∈2 is disposed. At a location corresponding to the location of sensing area 334a on the base layer 10', there is another sensing area 334b with an area A2. A distance between sensing areas 334a and 334b is d2. The accessory 335 of the sensor Q3 includes a sensing area 335a with an area A3, under which a dielectric material with dielectric constant ∈3 disposed. At a location corresponding to the location of sensing area 335a on the base layer 10', there is another sensing area 335b with an area A3. A distance between sensing areas 335a and 335b is d3. The capacitance of the capacitor formed by sensor Q1 is c1. The capacitance of the capacitor formed by sensor Q2 is c2. The capacitance of the capacitor formed by sensor Q3 is c3. At the same time, a transmission wire 444 is connected to 333a; a transmission wire 445 is connected to 334a; a transmission wire 446 is connected to 335a; a transmission wire 447 is connected to 333b; a transmission wire 448 is connected to 334b; and a transmission wire 449 is connected to 335b. The transmission wires 444, 445, and 446 are connected together to one input terminal of the signal processor 002. Transmission wires 447, 448, and 449 are connected together to the other input terminal of the signal processor 002. The capacitance of the sensor Q1 is c1 and changes with applied force. Thus, as long as the capacitances of Q1, Q2, and Q3 do not overlap, processor 002 would know which sensor is being pressed. In FIG. 16 the sensors are connected in parallel. The same can also be applied to serially connected sensors.

The Thirteenth Preferred Embodiment

Figure 22:
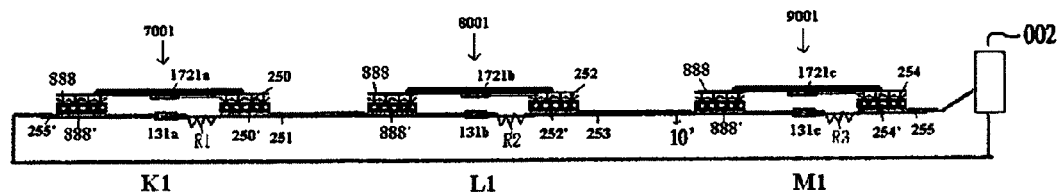
FIG. 22 shows a shematic diagram of the thirteenth preferred embodiment of the present invention.

Referring to FIG. 22, which shows a thirteenth preferred embodiment of the invention. This sensing apparatus comprises a base layer 10', and sensors K1, L1, and M1.

The accessory 7001 of the sensor K1 comprises a piece of non-electrically-conductive Velcro® as a substrate, which contains a sensing area 1721a that is lower than the thickness of the surrounding Velcro. The sensor K has output terminals 250 and 251, wherein the output terminal 250 is made of a piece of electrically-conductive Velcro®, and is connected to a conductive Velcro® 250" on a cloth material. Therefore, when the accessory and the cloth material are matched, output terminals 250 and 251 connect and remain connected. When the accessory 7001 is attached to the base layer, the Velcro 888 is "loop and hooked" by its counterpart 888' on the base layer 10, and the sensing area 1721a is electrically connected to terminal 251 through 250 and 250' and furthermore to the sensing area 131b of the sensor L1. The terminal 251 is also connected to a 100Ω resistor R1, which is serially connected to the sensing area 131a on the base layer 10' under the sensing area 1721a. When the accessory 7001 is pressed, both sensing areas 1721a and 131a contact to short circuit the R1. The sensing area 131a is also connected to the output terminal 255' and furthermore to one of the input terminals of the signal processor 002.

The accessory 8001 of the sensor L1 is comprised of a piece of non-electrically-conductive Velcro 888 as a substrate, a piece of electrically-conductive Velcro 252 as a output terminal, and a sensing area 1721a electrically connected to the Velcro 252, placed on the center of the two Velcro with lower altitude such that it can contact its conductive counterpart 252' on the base layer while pressed. The 252' is electrically connected to an output terminal 253. When the accessory 8001 is attached to the base layer, the Velcro 888 is "loop and hooked" by its counterpart 888' on the base layer 10, and the sensing area 1721b is electrically connected to terminal 253 through 252 and 252' and furthermore to the sensing area 131c of the sensor M1. The terminal 253 is also connected to a 300Ω resistor R2, which is serially connected to the sensing area 131b on the base layer 10' under the sensing area 1721b. When the accessory 8001 is pressed, both sensing areas 1721b and 131b contact to short circuit the R2.

The accessory 9001 of the sensor M1 is comprised of a piece of non-electrically-conductive Velcro 888 as a substrate, a piece of electrically-conductive Velcro 254 as a output terminal, and a sensing area 1721c electrically connected to the Velcro 254, placed on the center of the two Velcro with lower altitude such that it can contact its conductive counterpart 254' on the base layer while pressed. The 254' is electrically connected to an output terminal 255. When the accessory 9001 is attached to the base layer, the Velcro 888 is "loop and hooked" by its counterpart 888' on the base layer 10, and the sensing area 1721c is electrically connected to terminal 255 through 254 and 254' and furthermore to the input terminal of the signal processor 002. The terminal 255 is also connected to a 500Ωresistor R3, which is serially connected to the sensing area 131c on the base layer 10' under the sensing area 1721c. When the accessory 9001 is pressed, both sensing areas 1721c and 131c contact to short circuit the R3.

The sensors K1, L1, and M1 are thus serially connected to the input terminals 255 and 255' of the signal processor 002. When none of the sensors are pressed, the resistance in between the terminals 255 and 255' is 900Ω; when only K1 pressed, R1 is short circuited, thus the resistance is 800Ω; when only L1 pressed, R2 is short circuited, thus the resistance is 600Ω; when only M1 pressed, 400Ω; when both K1 and L1 pressed, 500Ω; when both K1 and M1 pressed, 300Ω; when both L1 and M1 pressed, 100Ω; when all sensors pressed, zero Q. None of the different condition give same resistance, thus the signal processor 002 can determine which sensor or sensors are pressed.

The Fourteenth Preferred Embodiment

Figure 23:
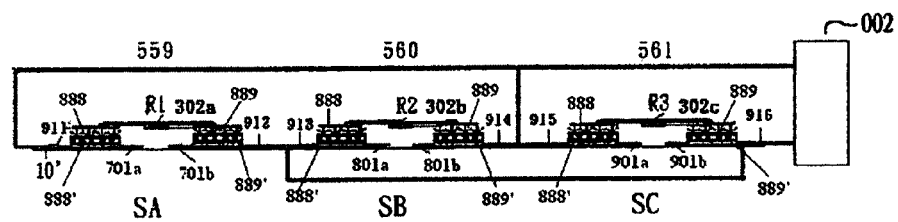
FIG. 23 shows a shematic diagram of the fourteen preferred embodiment of the present invention.

The fourteenth preferred embodiment is shown in FIG. 23, where the sensing apparatus is comprised of a base layer 10', and sensor SA, SB, and SC placed on the base layer 10' and electrically parallel connected by two transmission wires 911 and 916 to the signal processor 002. The accessory 559 of the sensor SA includes a sensing area 302a with a 1 KΩ resistor R1; the accessory 560 of the sensor SB includes a sensing area 302b with a 2 KΩ resistor R2; the accessory 561 of the sensor SC includes a sensing area 302bc with a 4 KΩ resistor R3. The sensing areas and resistors are fastened by Velcro 888 and 889, which are fixed by their counterpart Velcro 888' and 889' on the base layer.

Correspondent to the sensing area 302a, two terminals 701a and 701b are placed on the base layer, which are connected by transmission wires 911 and 912, respectively. Likewise to the sensing area 302b, two terminals 801a and 801b are placed on the base layer, which are connected by transmission wires 913 and 914, respectively. To the sensing area 302c, two terminals 901a and 901b are placed on the base layer, which are connected by transmission wires 915 and 916, respectively. The transmission wires 911, 913, and 915 are connected together to the signal processor as one of the input terminals. The transmission wires 912, 914, and 916 are also connected together to the signal processor as the other input terminals. When none of the sensor pressed, the resistance measured by the signal processor is infinite; when only sensor SA pressed, the sensing area 302a contacts both the terminal 701a and 701b, the resistance turns from infinite to 1 kΩ. When the forced goes out, the resistance goes back to infinite.

Alternatively, the resistor R1 in FIG. 23 can be connected directly to the terminal 701a and 701b instead; so can R2 to 801a and 801b, and R3 to 901a and 901b. In the mean while, the resistances of the sensing areas should be revised to approximate zero. Thus the sensing apparatus can give the same results.

By the configuration shown in FIG. 23, R1 can be a thermistor to measure the body temperature of the wearer. If the environment is so cold such that the body temperature is too low, then the signal processor can ignite a heater. When the sensor SA pressed, the signal processor 002 can measure the temperature of the position where the sensor SA placed. Thus, the sensor SA is not only a temperature sensor but also a pressure sensor. By the same principle, R1 can also be a photo resistor or color sensor which can reflect the intensity or color of incident light by its resistance. When pressed, the signal processor can determine whether the light is on or off, blue or red; and response accordingly. For example, when the light off, the signal processor 002 can turn on the LED on the shirt; when the light turns red, the signal processor 002 can turn on the blue LED. Thus, the sensor is not only a pressure sensor but also a photo or color sensor.

The threshold of the force that activates the sensor is determined by the structure and materials of the accessory and the Velcro, e.g., thickness, hardness, elasticity, and the area ratio of the Velcro over the accessory. Higher the ratio, high the elasticity, the thicker, the harder, then the threshold will be higher.

The structure of this embodiment can be the same to the eighth embodiment, to make a hat-shape accessory by plastic, latex rubber, silicone rubber, synthesized sponge, etc. The Velcro is to fix the accessory on the base layer, and the sensing area in the center of the accessory can be made of conductive silicone rubber to conduct the two terminals under the accessory.

The Fifteenth Preferred Embodiment

Figure 24:
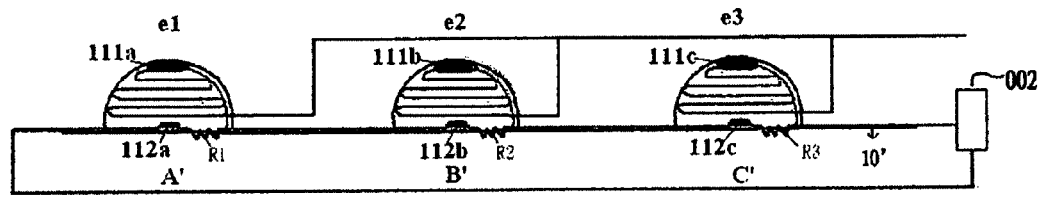
FIG. 24 shows a shematic diagram of the fifteenth preferred embodiment of the present invention.

The fifteenth preferred embodiment is shown in FIG. 24, where the sensing apparatus is based on the structure disclosed on the second preferred embodiment. The accessory e1 of the sensor A' is like a hemisphere, where the sensing area 111a on the accessory e1 or the sensing area 112a is a magnetic conductor that emits magnetic field lines, and transmission wires that made of steel fiber are stitched as a coil such that current can be induced while the hemisphere is pressed by an applied force. By the same principle, a magnetic conductor and a coil can be stitched around the clips shown in FIG. 7 to induce current by pulling the clip. This method can also be applied to other sensors B' and C', and copper wire or silver wires can also be used to form a coil like steel fiber.

The sensing apparatus can be applied to implement a physiological function signal detecting system, which is comprised of a said sensing apparatus which senses changes of the user's body and responses the posture changes by its circuit output; at least one detector to detect physiological function signal; and a signal processor that connects to the said sensing apparatus and detector, to receive the circuit output and the signal of the sensing apparatus, and to begin to record the signal according to a first criterion.

The preferred embodiment of a physiological function signal detecting system is shown in FIG. 17. The physiological function signal detecting system is comprised of a sensing apparatus, four physiological function signal detectors, and a signal processor 003, where the sensing apparatus is comprised of a base layer 10', sensor A4, B4, C4, and D4, and two output terminals 91 and 98.

The sensor A4 is comprised of a sensing area 555b placed on the base layer 10', an accessory 555 placed above the sensing area 555b, and two output terminals 91 and 92. The hemisphere-shape accessory 555 is comprised of a sensing area 555a correspondent to the sensing area 555b on the base layer 10', and a 100Ω resistor connected to 555a and the output terminal 92, which is also connected to the sensing area 555b, and the output terminal 91 connected to the other end of the sensing area 555a. The accessory 555 is made of elastic material such that the sensing area 555a can contact 555b to short circuit R1 while pressed, and it goes back without contacting while the applied force is gone.

The structures of the sensor B4, C4, and D4 are same as A4, while their resistors are 200Ω, 400Ω, and 800Ω.

The output terminals of the sensors are serially connected, i.e., 92 to 93, 94 to 95, 96 to 97, to form a circuit with the output terminal 91 and 98 to the signal processor 003. The sensing apparatus described above can sense the movement of the wearer and output a unique resistance to the signal processor accordingly.

The four physiological function signal detectors are placed in the four sensors A4, B4, C4, and D4. Each physiological function signal detector is comprised of a sensing area on the base layer (K2, M2, N2, and F2), a sensing area on the accessory (K1, M1, N1, and F1), and an output transmission wire (81, 82, 83, 84) connected to the sensing area on the accessory. The 81 and 83 are connected together to the signal processor 003, so are 82 and 84, and the four sensors A4, B4, C4, and D4. The signal processor 003 also measures the resistance in between terminal 91 and 98 to determine the movement or posture of the wearer, and then selects the physiological function signal to record according to a first criterion.

In practical application, the physiological function signal can be but not limit to electrocardiogram, heartbeat, heart sound and lung sound, respiration (including thoracic breathing, abdominal breathing, thoracic and abdominal combined breathing), Oxygen saturation, body temperature, sweatiness, blood pressure, electromyogram, body impedance, body movement, etc.

The present physiological function signal detecting system can be applied to detect the electrocardiogram during sleep. The sensor A4 and B4 are placed on the correspondent position of the right and left chest of the wearer of the pajamas. The sensor C4 and D4 are placed on the correspondent position of the right and left back of the wearer of the pajamas. When the wearer lies on supine position, the sensor C4 and D4 are pressed to output a resistance such that the signal processor 003 can determine the posture of the wearer and initiate the K1 and M1 to detect the electrocardiogram of the wearer according to the first criterion, that is, initiates K1 and M1 when the resistance is 1200Ω. By the same principle, when the resistance is 300Ω, the signal processor initiates N1 and F1. Thus, the physiological function signal system not only can record the sleeping posture but also detect electrocardiogram. By the same principle, it can also be applied to detect electromyogram, electroencephalogram, and biological element.

In FIG. 17, the sensing area K1 can be a photo sensor, humidity sensor, or temperature sensor, by which the light or temperature can be detected. In this application, K2 is not necessary. By the same principle, K2 is necessary while K1 is not in some application. For example, K2 is a thermistor to detect the temperature of the contact position, or an ultrasonic probe to observe the inside body, or a microphone to detect heart sound or lung sound, such as temperature of the armpit or chest heart sound. In this application, a independent transmission wire necessary to send the signal to the signal processor 003. In addition, the sensing area K2 can be a heating wire to keep the body warm. In another application, the sensing areas K2 and M2 can be electrodes connected to the signal processor by two independent wires to give transcutaneous electrical nerve stimulation (TENS) or electrical shock when necessary.

The Sixteen Preferred Embodiment

Figure 25:
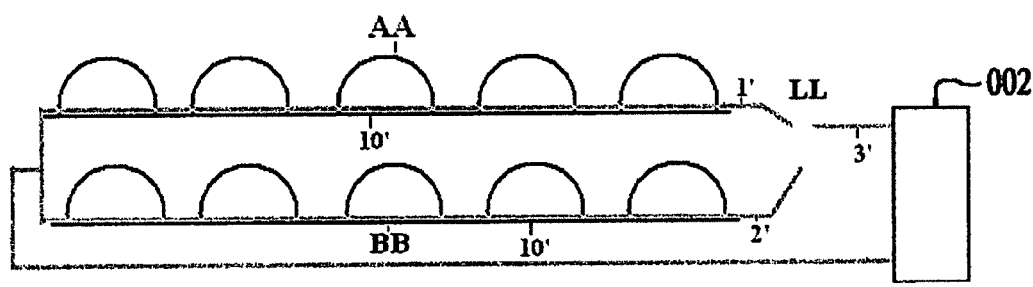
FIG. 25 shows a shematic diagram of the sixteenth preferred embodiment of the present invention.
Figure 25A:
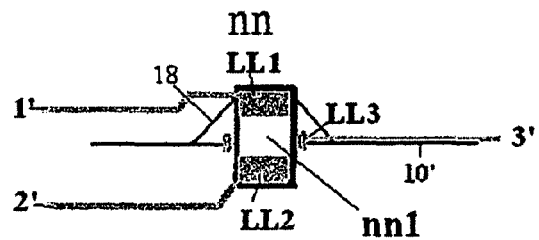
FIG. 25A~25D show shematic diagrams of a switch of the present invention.

The sixteen preferred embodiment is shown in FIG. 25, where the sensing apparatus is comprised of a base layer 10', a sensor group AA, a sensor group BB, a single-pole double-throw switch LL, and a signal processor 002.

Both sensor group AA and BB are comprised of five electrically connected sensors. The sensor group AA and BB use a common transmission wire to connect to the signal processor 002. Individually, the sensor group AA is connected to the switch LL by a transmission wire 1' and BB to LL by another transmission wire 2'. The switch LL is connected to the signal processor 002 by a transmission wire 3'. In the present embodiment, within the tolerance error of the resistors, the number of the sensor in a group can be increased.

The switch LL selects sensor group AA or BB to connect to the signal processor 002, and the structure of which is shown in FIG. 25. The switch includes an accessory nn which is comprised of a column nn1 and two connectors 18 to constrain the column nn1 in an open on the base layer 10'. The column nn1 includes two separate conductors LL1 and LL2 and a conductor LL3 is placed on the side of the open, where conductor LL1 is connected by the transmission wire 1', LL2 by 2', and LL3 by 3'. When a force applied, the column nn1 can be moved accordingly such that LL1 is electrically connected to LL3, or LL2 to LL3. The switch LL can be stitched on a shirt or pants such that it switches according to the wearer's body motion.

Figure 25B:
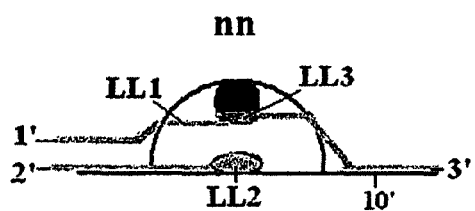

Another structure of the switch LL is shown in FIG. 25B, where the hat-shaped accessory nn includes a conductor spring LL1 and conducting area LL3, and a conducting area LL2 placed on base layer 10' at the correspondent position to LL3. The transmission wires 1', 2' and 3' are connected to the LL1, LL2, and LL3, respectively. Without a force applying, the conducting area LL3 is connected to LL1 and not to LL2. When a force applied, LL3 moves downwards to leave LL1 and contact LL2.

Figure 25C:
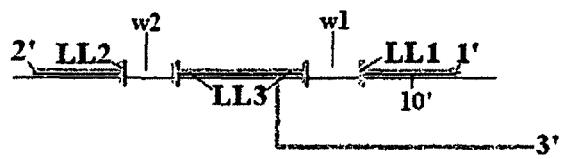

Another structure of the switch LL is also shown is FIG. 25C, where switch is comprised of two parallel connected clips on the base layer 10', where the clip w1 has two conducting area, LL1 and LL3, at both end, so does w2, LL2 and LL3. The transmission wires 1', 2' and 3' are connected to the LL1, LL2, and LL3, respectively. When the applied tension force opens the clip w1 but not w2, LL2 is connected to LL3, thus the sensor group BB was selected to connect the signal processor. When the applied tension force opens the clip w2 but not w1, LL1 is connected to LL3, thus the sensor group AA was selected to connect the signal processor. Without force applied, both clips are close, which means it is not used by the wearer. When both clips are pulled open, the applied force may be too large, or one or components malfunctioned.

Figure 25D:
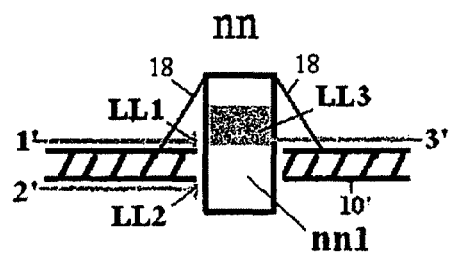

Another structure of the switch LL is also shown is FIG. 25D, where switch includes an accessory nn, which is comprised of a column nn1 and two connectors 18 to constrain the column nn1 on the base layer 10'. The column nn1 includes a conductor LL3, and another two conductors LL1 and LL2 are placed on the upper layer and lower layer of a open on the base layer 10', where LL1 is connected with the transmission wire 1', LL2 with 2', and LL3 with 3'. When a force applied to the column nn1, the column will move accordingly such that either LL1 or LL2 may contact LL3. Thus, two groups of sensors can be selected by the switch LL to connect to the signal processor through only two transmission wires, where the switch LL is controlled by the body movement of the wearer.

The Seventeen Preferred Embodiment

Figure 26:
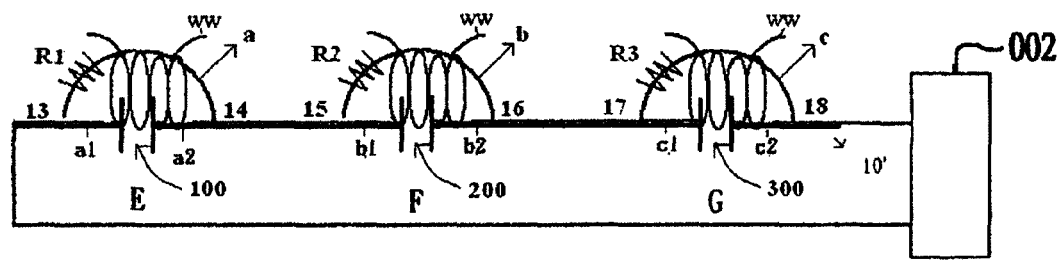
FIG. 26 shows a shematic diagram of the seventeenth preferred embodiment of the present invention.

The seventeen preferred embodiment is shown in FIG. 26, where the structure of the sensing apparatus is disclosed by the third preferred embodiment. The sensing areas a1 and a2 of strain gauge E is made of conductive magnet, such as Nd—Fe—B alloy, and two coils are stitched on the accessory a and base layer 10' around the clip 100. Thus, when the strain gauge E is distorted by a force, current can be induced though the coils, and so do sensor F and G.

The resistors in FIG. 26 can be made of conductive rubber, graphite powder, carbon fiber, nano carbon tube, etc. The resistance of a material is $R=\rho L/A$, where $\rho$ is the material resistance coefficient, L is the length, and A is the cross-sectioned area. Different resistances can be implemented by choosing length, cross-sectioned area, and the material. For example, choosing the thickness of a carbon or metal film, or lengthen the resistor by stitching the resistor with a z pattern.

Resistors and capacitors are used to describe the embodiments; however, other components can also be used, such as inductors. As long as each sensor output is unique, and each circuit output of the combinations of sensor is different from the others, the signal processor can determine which one sensor or sensors are pressed or pulled without mix up.

THE FIRST EXAMPLE OF APPLICATION

Figure 18:
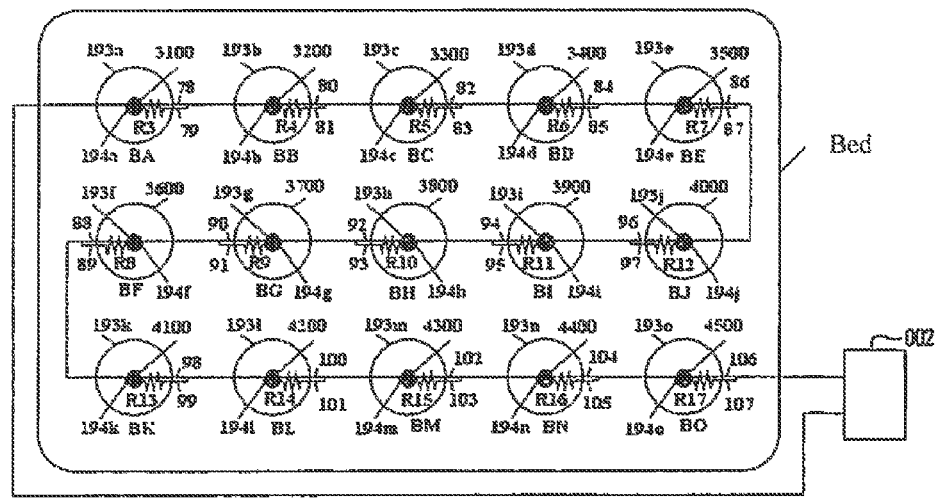
FIG. 18 shows a shematic diagram of the preferred embodiment of the bed sheet by the present invention.

FIG. 18 shows the schematic diagram of the application of the present invention on a body sensing bed sheet, which includes a base layer and fifteen sensors, which are serially connected such that only two terminals are necessary to connect to the signal processor 002. The signal processor uses only one ohmmeter to detect which one sensor or sensors are pressed such that the posture or movement of the sleeper can be analyzed. All transmission wires do not overlap such that it is very easy to manufacture, operate, and maintain. This structure can be also applied in keyboard, control panel, seat, cushion, etc.

THE SECOND EXAMPLE OF APPLICATION

Figure 19:
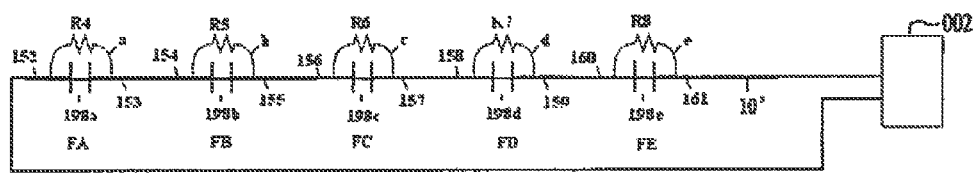
FIG. 19 shows a shematic diagram of the preferred embodiment of the belt by the present invention.

FIG. 19 shows the schematic diagram of the application of the present invention on a breath sensing belt, which includes a base layer 10' and five sensors FA, FB, FC, FD, and FE. Each sensor is comprised of an accessory (a, b, c, d, and e), a resistor (R4, R5, R6, R7, and R8), and a clip (198*a* to 198*e*). The threshold tension forces to pull open the clips are 100, 150, 200, 250, and 300 grams for each clip, respectively; so are the resistance 2K, 4K, 8K, 16K, and 32K for each resistor. The signal processor 002 needs only a ohmmeter and two terminals to measure the tension force by five segments. It's easy to manufacture, maintain, and operate.

THE THIRD EXAMPLE OF APPLICATION

Figure 20:
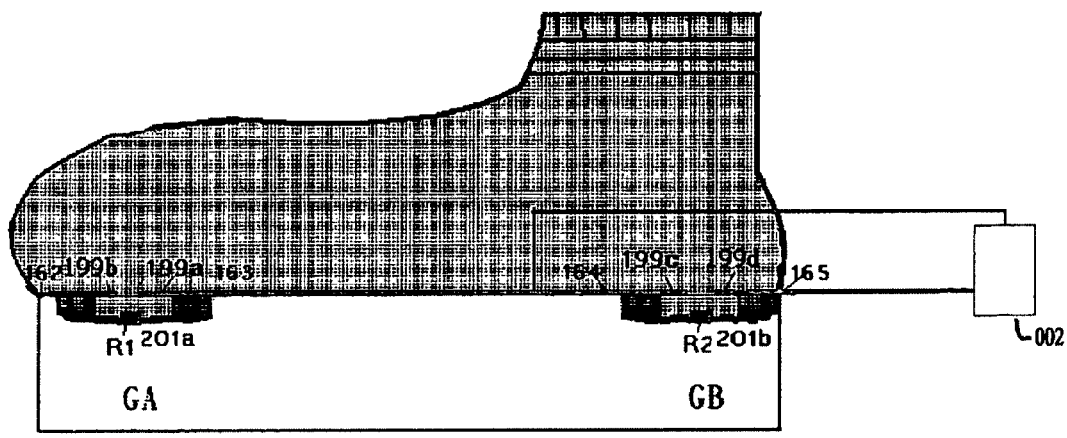
FIG. 20 shows a shematic diagram of the preferred embodiment of the socks and shoes by the present invention.

FIG. 20 shows the schematic diagram of the application of the present invention on a gait sensing sock, which includes a base sock and two sensors GA and GB that are electrically connected to the signal processor 002. Thus the signal processor 002 can record and analyze the gait of the wearer.

THE FORTH EXAMPLE OF APPLICATION

Figure 21:
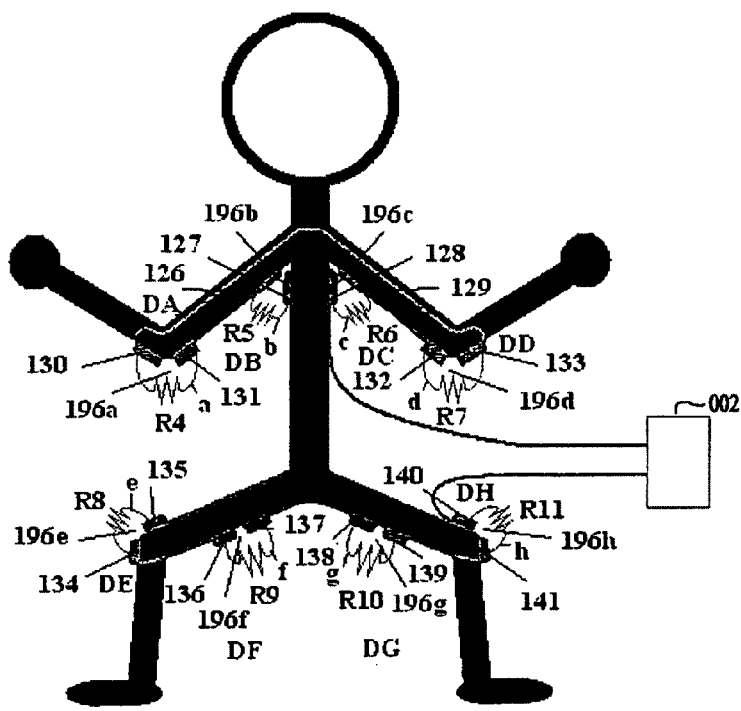
FIG. 21 shows a shematic diagram of the preferred embodiment of the suit and pants present invention.

FIG. 21 shows the schematic diagram of the application of the present invention on a shirt and pants, which include base layers and eight sensors DA to DH that are serially connected such that only two terminals are used to connect to the signal processor 002. Only one ohmmeter is needed to detect the states of each sensor. Thus the body movements or postures of the wearer, such as walking, sitting, lying, swimming, bending, sleeping, driving, and biking, can be determined.

The present invention has the following advantages:

1. Conventional stitching or gluing techniques are used to fix sensors on base layer, just like ordinary garment or leather. It is washable, easy to assemble and disassemble.

2. Only one circuit is necessary, and the wires does not overlap, i.e., no interlacing, such that easy to manufacture.

3. Only a few wires are necessary such that the wires can go along the seams or joints on garments, bed sheet, and cushion. It is hard to see the wires.

4. Only a few components are used in the present invention, such that the weight increased is very light. Thus, the wearer will not feel heavy or uncomfortable.

5. The non-washable components, such as the signal processor, battery, Bluetooth module, are connected to the washable components by a detachable connector such that the sensors and the transmission wires are fully washable and they can be washed together with the garment.

6. The present invention can allocate the malfunction component, such that it is easy to maintain and repair.

7. The terminal of the sensor circuit can be connected by conventional parts that are widely used in textile industry, such as hook, button, magnetic button, Velcro, etc. It is fully compatible to garment.

8. LEDs can be installed in the sensors to indicate which sensor or sensors are activated, or malfunction.

9. All wires can be installed on the base layer, not on the accessory. Thus, the whole circuit is on the base layer such that it is simple and easy to manufacture.

10. Another sensing area can be installed nearby or on the outer surface of an accessory while not connected to the sensor. Thus, when a force activates the sensor, the said sensing area can still give physiological function signals from the position of the activated sensor, such as electrocardiogram, body temperature, electromyogram, biological element, electroencephalogram, lung sound, heart sound, ultrasound, environmental temperature, light, sweatiness, etc.

11. An electrode pad or a heating pad can be installed nearby or on the outer surface of an accessory while not connected to the sensor. Thus, when a force activates the sensor, the said pad can heat up the body or give electrical therapy such as TENS or electrical shock.

12. The pressure and strain gauge shown above can be used to detect the posture, movement, breath, gait, falling, and action while sleeping of the wearer.

13. The sensor can give more than one physiological function signals, such as body temperature, breath, heartbeat, sweatiness, light, sound, and posture. The user of the present invention can easily customize it by just install the sensor or sensors in need without buying a whole new product.

Shown above are only the examples of preferred embodiments, it is not to limit the present invention in any form. Although the preferred embodiments have been disclosed above, they should not be used to limit the range of the present invention. Any person, who is familiar with this professional technology, can utilize the content of the disclosed invention with modification or variation within the scope of the technological scheme of the disclosed invention to implement an equivalent embodiment. However, any form of modification or variation done to the disclosed invention, is still within the scope of the technological scheme of the disclosed invention.

What is claimed is:

1. A sensing apparatus comprising:
a base layer, and;
a plurality of sensors disposed on the base layer, wherein the plurality of sensors are connected to form a circuit with two output terminals configured to output a circuit output that varies with a force applied on one or more sensors in the plurality of sensors; wherein each of the plurality of sensors is configured to output a unique sensor output value such that a sensor output value of any one sensor of the plurality of sensors is different from a sensor output value of any other sensor of the plurality of sensors, and a sum of any one or more sensor output values is different from a sum of any other one or more sensor output values.

2. The sensing apparatus of claim 1, further comprising a signal processor connected to the output terminals for detecting the circuit output.

3. The sensing apparatus of claim 2 wherein the signal processor can identify one or more locations on the base layer of one or more sensors among the plurality of sensors that produce the circuit output.

4. The sensing apparatus of claim 1 wherein the base layer is made of textile or leather.

5. The sensing apparatus of claim 1, wherein the plurality of sensors comprise one or more of the following: a pressure sensor, a strain gauge, a switch, a humidity sensor, an ultrasound sensor, a microphone, a photo sensor, and a temperature sensor.

6. The sensing apparatus of claim 1, wherein the sensor has a protective device to prevent the structures of the sensor from being destroyed by excessive force.

7. The sensing apparatus of claim 1, wherein the sensor includes:
a first sensing area disposed on the base layer;
an accessory disposed above the first sensing area on the base layer;
a second sensing area disposed on the accessory at a position corresponding to a position of the first sensing area; and
an electronic component electrically connected to the first or second sensing areas.

8. The sensing apparatus of claim 7, wherein the sensor includes one of the following: a resistor, a capacitor, and an inductor.

9. The sensing apparatus of claim 1, wherein the sensor comprises a light-emitting-diode to indicate which sensor or sensors are activated or malfunctioning.

10. A physiological function detecting system, comprising:
- a sensing apparatus for sensing a posture change of a user's body, wherein the sensing apparatus comprises a base layer and a plurality of sensors disposed on the base layer, wherein the plurality of sensors are connected to form a circuit with two output terminals configured to output a circuit output that varies with a force applied on one or more sensors in the plurality of sensors; wherein each of the plurality of sensors is configured to output a unique sensor output value such that a sensor output value of any one sensor of the plurality of sensors is different from a sensor output value of any other sensor of the plurality of sensors, and a sum of any one or more sensor output values is different from a sum of any other one or more sensor output values;
- a detector to detect a physiological function or a treatment device; and
- a signal processor connected to the plurality of sensors and the detector to receive a signal from one or more of the plurality of sensors, and to trigger the detector to detect the physiological function or to trigger the treatment device according to a first criterion.

11. The physiological function signal detecting system of claim 10, wherein the physiological function signal detecting system comprises the treatment device.

12. The physiological function detecting system of claim 11, wherein the treatment device is a heater, a transcutaneous electrical nerve stimulator, an ultrasonic device, or an electrical shock device.

13. A sensing apparatus, comprising:
- a base layer, comprising a first sensing area, and;
- an accessory based on a hook-and-loop fastener, comprising a second sensing area at a position corresponding to a position of said first area, and a counterpart hook-and-loop fastener placed on the base material layer at a position corresponding to the position of the second sensing area, wherein the first and the second sensing areas are connected, and wherein a state of connection varies with an applied force in a force-strength dependent manner that various states correspond to different strengths of the applied force.

14. The sensing apparatus of claim 13, wherein the conducting circuit is implemented by a conductive hook-and-loop fastener.

15. A sensing apparatus, comprising:
- a base layer, comprising a first sensing area; and
- an extender comprising an accessory and a connecting part, wherein the connecting part is to connect the accessory to the base layer;
- a second sensing area is disposed on the extender at a position corresponding to a position of the first sensing area on the base layer, wherein the first and the second sensing areas are connected such that a state of the connection varies with an applied force, and the first and second sensing areas contain a magnet material such that the first sensing area and the second sensing area are inductively coupled, and a condition of inductive coupling is adapted to be changed by an outside force.

16. The physiological function detecting system of claim 10, wherein the physiological function is selected from the group consisting of EKG function, heart rate, pulmonary function, respiration, blood oxygen concentration, body temperature, sweat function, blood pressure, muscle electrograph, body resistance, concentrations of biological elements, and limb movement.

17. The sensing apparatus of claim 15, wherein the accessory is surrounded by a coil and a current is induced in the coil when a force is applied.

18. The sensing apparatus of claim 15, wherein the connecting part is a hook-and-loop fastener.

19. The sensing apparatus of claim 15, wherein another detecting sensor is installed nearby or on the outer surface of the accessory.

* * * * *